United States Patent [19]

Ghebre-Sellassie et al.

[11] Patent Number: 4,925,676
[45] Date of Patent: May 15, 1990

[54] EXTENDED RELEASE GEMFIBROZIL COMPOSITION

[75] Inventors: Isaac Ghebre-Sellassie, Stanhole; Uma Iyer, Mendham; Mahdi B. Fawzi, Flanders, all of N.J.

[73] Assignee: Warner-Lambert Company, Ann Arbor, Mich.

[21] Appl. No.: 305,083

[22] Filed: Feb. 2, 1989

[51] Int. Cl.5 ............................................. A61K 9/26
[52] U.S. Cl. .................... 424/470; 424/468; 424/469; 424/497
[58] Field of Search ............... 424/468, 469, 470, 497

[56] References Cited

U.S. PATENT DOCUMENTS

| | | | |
|---|---|---|---|
| 4,132,753 | 1/1979 | Blichare et al. | 264/25 |
| 4,195,084 | 3/1980 | Ong | 424/238 |
| 4,263,272 | 4/1981 | Frigerio | 424/19 |
| 4,291,016 | 9/1981 | Nougaret | 424/35 |
| 4,533,562 | 8/1985 | Ikegami et al. | 427/3 |
| 4,661,162 | 4/1987 | Kurihara et al. | 106/169 |
| 4,716,033 | 12/1987 | Denick, Jr. | 424/48 X |
| 4,778,676 | 10/1988 | Yang et al. | 424/478 |
| 4,814,354 | 3/1989 | Ghebre-Sellassie et al. | 424/440 |
| 4,816,264 | 3/1989 | Phillips et al. | 424/468 |

FOREIGN PATENT DOCUMENTS 2554717  5/1985  France .
2179254  3/1987  United Kingdom .

*Primary Examiner*—Thurman K. Page
*Attorney, Agent, or Firm*—Mathews, Woodbridge & Collins

[57] ABSTRACT

A disintegratable gemfibrozil tablet providing both immediate and enteric release is compressed from a mixture of a first granulation of gemfibrozil with at least one acid-disintegratable binder and a second granulation formed from the first granulation but regranulated or coated with an alkali-disintegratable formulation of at least one substantially alkali-soluble and substantially acid-insoluble polymer.

10 Claims, No Drawings

EXTENDED RELEASE GEMFIBROZIL COMPOSITION

The present invention relates to enteric release gemfibrozil formulations.

BACKGROUND

Gemfibrozil, or 5-(2,5-dimethylphenoxy)-2,2-dimethylpentanoic acid, is a widely used antihyperlipoproteinemic agent. While apparently absorbed throughout the gastrointestinal tract, maximum absorption appears to occur in the upper gastrointestinal tract and this is true notwithstanding the poor solubility of the drug at acidic pH.

Prior attempts at developing sustained release formulations, as for example reservoir systems, have not met with a great deal of success, producing either inadequate bioavailability or unacceptable release profiles. Paradoxically, it appears the achievement of a sustained release formulation requires disintegration or erosion in the stomach and upper gastrointestinal tract.

British Application No. 2,179,254 discloses compositions of analgesic propionic acid derivatives (such as ibuprofen) coated with a methacrylic-acrylic copolymer, then with a methacrylic ester copolymer, and finally with a mixture of polysorbate 80 and hydroxypropyl methylcellulose.

EPO-A No. 8600802 discloses sustained release compositions of polyethylene glycol and an amphiphilic compound.

French Application No. 2,554,717 discloses sustained release compositions which employs as the matrix a vinylpyrrolidone-vinyl acetate copolymer and an acrylic polymer cross-linked with polyallyl sucrose. (See also Belgian application No. 901007.)

U.S. Pat. No. 4,132,753 discloses controlled release granules in which the powdered medicament is heated so as to sink into a finely divided wax material.

U.S. Pat. No. 4,195,084 discloses a liquid suspension of finely ground tall oil sitosterols for use in reducing hypercholesteraemia.

U.S. Pat. No. 4,263,272 discloses three component formulations of bile acids which release gradually or in two stages.

U.S. Pat. No. 4,291,016 discloses pharmaceutical compositions having a matrix core coated with hydroxypropyl methyl cellulose.

U.S. Pat. No. 4,533,562 discloses tablets coated with a film-forming polymer such as hydroxypropyl methylcellulose and a liquid plasticizer such as polyethylene glycol.

U.S. Pat. No. 4,661,162 discloses an enteric soluble composition containing a mixture of an enteric-soluble polymer such as (m)ethyl acrylate/methacrylate copolymers and a polyanionic polymer such as alginic acid and its salts.

DETAILED DESCRIPTION

The present invention relates to a disintegratable formulation of gemfibrozil providing both immediate and enteric release. By enteric release is meant release in the alkali environment of the intestinal tract without substantial release in the acidic environment of the stomach.

Specifically the invention comprises a tablet compressed from a mixture of at least a first and second granulation. The first granulation comprises finely divided particles of pure gemfibrozil or a powder blend of gemfibrozil with excipients granulated with at least one acid-disintegratable cellulose material. The second granulation comprises the first granulation regranulated or coated with an alkali-disintegratable formulation. The alkali-disintegratable formulation comprises at least one polymer which is substantially alkali-soluble and substantially acid-insoluble.

The first granulation comprises finely divided particles of pure gemfibrozil or a powder blend of gemfibrozil with excipients granulated with at least one acid-disintegratable binder such as a cellulose derivative or polyvinyl pyrrolidone. Suitable cellulose derivatives include microcrystalline cellulose, water soluble hydroxyalkylcelluloses such as hydroxyethyl cellulose, hydroxypropyl cellulose, and hydroxypropyl methyl cellulose. Mixtures of the cellulose derivatives are particularly preferred.

The second granulation comprises the first granulation of gemfibrozil either coated or regranulated with at least one polymer which is substantially alkali-soluble and substantially acid-insoluble. Suitable alkali-soluble and acid-insoluble polymers include cellulose phthalates, polyvinyl phthalates, cellulose succinates, cellulose butyrates, poly(meth)acrylic acids, and partially esterified poly(meth)acrylic acids. Particularly preferred are cellulose phthalates and partially esterified poly(meth)acrylic acids.

The use of "meth" as a prefix in parenthesis for the (meth)acrylic copolymers indicates that the polymer molecule is derived from one or both of acrylic and methacrylic species. Thus, the copolymer can be derived from partially esterified acrylic acid and methacrylic acid in which the ester groups are methyl and ethyl. Other conventional comonomers may be present in the copolymers as long as they do not detract from the copolymer's usefulness in the present system. Particularly useful is Eudragit L30D, a copolymer anionic in character based on partially esterified poly(meth)acrylic acid (ratio of free carboxy groups to esterified carboxy groups being about 1:1) and having a mean molecular weight of about 250,000.

The granulations of the first and second components are carried out sequentially. In each case wet granulation techniques are followed, using water and a small amount of a surfactant, as for example sodium lauryl sulfate. Following the initial granulation, a portion is either regranulated with the substantially alkali-soluble, acid-insoluble polymer, optionally together with a plasticizer such as triethyl citrate and an antifoam emulsion, or coated with the substantially alkali-soluble, acid-insoluble polymer.

The first and second granulations are then combined in a ratio of each to the other of from about 10:1 to about .1:10, respectively. This ratio can be varied to produce a desired release profile. The two granulations are mixed with one or more disintegration excipients operable to effect disintegration of the tablet in the stomach. Suitable disintegration excipients include one or more water dispersible cellulose derivatives such as microcrystalline cellulose, sodium croscarmelose, starch, starch derivatives such as sodium carboxymethylstarch, and cross-linked polyvinyl pyrrolidone.

Processing aids such as separating agents, plasticizers, stabilizers, lubricants and the like can be added in relatively minor amounts. Useful separating or anti-tackiness agents include kaolin, talc, magnesium trisilicate, silicon dioxide, calcium carbonate and the like. Talc is preferred. Lubricants including magnesium stearate, calcium stearate, zinc stearate, colloidal silicon dioxide, stearic acid, and polyethylene glycol also can be added to assist in the formulation.

Alternatively, the two granulations, formulated independently, are compressed in a two layer tablet then using a two layer press punch. Layer 1 consisting of the first granulation is first compressed and layer 2 consisting of the second granulation then is compressed over the first layer. Similarly the second granulation can be compressed as an inner core with the first granulation compressed about the core.

The tablets then are coated. The coating material is one whose solubility characteristics make it insoluble in the mouth but readily soluble in the acid environment of the gastric juices of the stomach. For handling and packaging purposes, it is preferred that the coating substance is polymeric in nature. However, other types of coating materials conventional in the pharmaceutical art can be substituted for all or part of the polymeric coating.

The following examples will serve to further typify the nature of the invention but should not be construed as being a limitation on the scope thereof, which scope is defined solely by the appended claims.

EXAMPLE 1

First Granulation

A first granulation is prepared from the following components:

| Ingredient | Parts by weight |
| --- | --- |
| Gemfibrozil | 750.00 |
| Microcrystalline cellulose | 60.00 |
| Hydroxypropyl cellulose | 15.00 |
| Sodium lauryl sulfate | 3.74 |
| Purified water | 147.50 |

The foregoing ingredients are mixed and granulated.

Second Granulation

A second granulation then is prepared from the following components:

| Ingredient | Parts by weight |
| --- | --- |
| 1st Granulation | 414.37 |
| Hydroxypropyl methyl cellulose phthalate | 102.35 |
| Hydroxypropyl cellulose | 3.39 |
| Triethyl citrate | 31.08 |
| Sodium lauryl sulfate | 0.46 |
| Antifoam AD emulsion | 0.41 |
| Purified water | 493.27 |

Final Formulation

The final tablet formulation then is prepared from the following components:

| Ingredient | Parts by weight |
| --- | --- |
| 1st Granulation | 414.37 |
| 2nd Granulation | 552.60 |
| Microcrystalline cellulose | 73.03 |
| Sodium croscarmelose | 50.00 |
| Talc | 5.00 |
| Calcium stearate | 5.00 |

The final blend (approximately 1100 parts by weight) is employed to compress tablets which can in turn be film coated by conventional techniques.

EXAMPLE 2

First Granulation

A first granulation is prepared as described in Example 1.

Second Granulation

A second granulation then is prepared from the following components:

| Ingredient | Parts by weight |
| --- | --- |
| 1st Granulation | 414.37 |
| Eudragit L30D (30% solids) | 363.36 |
| Triethyl citrate | 28.74 |
| Antifoam AD emulsion | 0.41 |
| Purified water | 237.91 |

Final Formulation

The final tablet formulation then is prepared from the following components:

| Ingredient | Parts by weight |
| --- | --- |
| 1st Granulation | 414.37 |
| 2nd Granulation | 552.53 |
| Microcrystalline cellulose | 73.10 |
| Sodium croscarmelose | 50.00 |
| Talc | 5.00 |
| Calcium stearate | 5.00 |

The final blend (approximately 1100 part by weight) is employed to compress tablets which can in turn be film coated by conventional techniques.

EXAMPLE 3

Tablets prepared according to Examples 1 and 2 were evaluated for their dissolution rate at pH 7.5 employing a USP II apparatus. Six aliquots were employed. The average figures observed for % of active ingredient dissolved are as follows:

| Composition | % Active Ingredient | |
| --- | --- | --- |
|  | 30 minutes | 60 minutes |
| Example 1 | 77.4 | 98.6 |
| Example 2 | 82.6 | 96.9 |

What is claimed is:

1. A disintegratable formulation of gemfibrozil providing both immediate and enteric release and comprising a tablet compressed from a mixture of at least a first and second granulation, said first granulation comprising finely divided particles of gemfibrozil granulated with at least one acid-disintegratable binder and said second granulation comprising said first granulation regranulated or coated with an alkali-disintegratable formulation comprising at least one polymer which is substantially alkali-soluble and substantially acid-insoluble.

2. A composition according to claim 1 wherein said alkali-soluble and acid-insoluble polymer is selected from the group consisting of cellulose phthalates, polyvinyl phthalates, cellulose succinates, cellulose butyrates, poly(meth)acrylic acids, and partially esterified poly(meth)acrylic acids.

3. A composition according to claim 2 wherein said alkali-soluble and acid-insoluble polymer is a hydroxyalkyl methylcellulose phthalate or a partially esterified poly(meth)acrylic acid.

4. A composition according to claim 3 wherein said (meth)acrylate copolymer is a anionic copolymer derived from partially esterified acrylic and methacrylic acid in which the ester groups are methyl and ethyl which has a mean molecular weight of about 250,000.

5. A composition according to claim 1 wherein said acid-disintegratable binder of said first granulation is a cellulose material or a polyvinyl pyrrolidone.

6. A composition according to claim 1 wherein said acid-disintegratable binder of said first granulation includes microcrystalline cellulose and hydroxypropyl cellulose.

7. A composition according to claim 1 wherein said acid-disintegratable binder of said first granulation is polyvinyl pyrrolidone.

8. A composition according to claim 1 wherein said tablet include one or more water dispersible cellulose derivatives as disintegration excipients.

9. A composition according to claim 8 wherein said disintegration excipients are selected from the group consisting of microcrystalline cellulose, sodium croscarmelose, starch, sodium carboxymethyl starch, and cross-linked polyvinyl pyrrolidone.

10. A composition according to claim 9 wherein said disintegration excipients are microcrystalline cellulose and sodium croscarmelose.

* * * * *